·

US007615666B2

(12) United States Patent
Nishimura et al.

(10) Patent No.: US 7,615,666 B2
(45) Date of Patent: *Nov. 10, 2009

(54) PROCESS FOR PRODUCTION OF TERTIARY AMINES

(75) Inventors: Toru Nishimura, Wakayama (JP); Atsushi Hirota, Wakayama (JP); Shoji Hasegawa, Wakayama (JP)

(73) Assignee: Kao Corporation, Tokyo (JP)

( * ) Notice: Subject to any disclaimer, the term of this patent is extended or adjusted under 35 U.S.C. 154(b) by 93 days.

This patent is subject to a terminal disclaimer.

(21) Appl. No.: 11/911,032

(22) PCT Filed: Apr. 6, 2006

(86) PCT No.: PCT/JP2006/307799

§ 371 (c)(1),
(2), (4) Date: Oct. 9, 2007

(87) PCT Pub. No.: WO2006/109848

PCT Pub. Date: Oct. 19, 2006

(65) Prior Publication Data

US 2009/0030236 A1 Jan. 29, 2009

(30) Foreign Application Priority Data

Apr. 7, 2005 (JP) .............................. 2005-110499

(51) Int. Cl.
*C07C 209/16* (2006.01)
*C07C 209/60* (2006.01)
(52) U.S. Cl. ....................................... 564/479; 564/480
(58) Field of Classification Search .................. None
See application file for complete search history.

(56) References Cited

U.S. PATENT DOCUMENTS

| 4,806,287 A | 2/1989 | Šulc et al. |
| 4,851,580 A | 7/1989 | Mueller et al. |
| 6,506,361 B1 | 1/2003 | Machado et al. |
| 7,351,866 B2 * | 4/2008 | Hirota et al. ................. 564/479 |
| 2003/0207761 A1 | 11/2003 | Ding |
| 2005/0129594 A1 | 6/2005 | Welp et al. |
| 2005/0283025 A1 | 12/2005 | Hirota et al. |
| 2006/0135815 A1 | 6/2006 | Oguri et al. |
| 2007/0179320 A1 | 8/2007 | Hirota et al. |

FOREIGN PATENT DOCUMENTS

| EP | 0 227 904 A1 | 7/1987 |
| EP | 0 281 417 A2 | 9/1987 |
| EP | 0 588 192 A1 | 3/1994 |
| EP | 1 358 935 A1 | 11/2003 |
| JP | 62 114940 | 5/1987 |
| JP | 62-114940 | 5/1987 |
| JP | 64-13060 | 1/1989 |
| JP | 6413064 | 1/1989 |
| JP | 6-211754 | 8/1994 |
| JP | 2002-35569 | 2/2002 |
| JP | 2003-176255 | 6/2003 |
| JP | 2003 340283 | 12/2003 |
| JP | 2003-340283 | 12/2003 |
| JP | 2005-349319 | 12/2005 |
| JP | 2005 349319 | 12/2005 |
| JP | 2006-102709 | 4/2006 |
| JP | 2006 102709 | 4/2006 |

OTHER PUBLICATIONS

U.S. Appl. No. 12/159,094, filed Jun. 25, 2008, Hasegawa, et al.

\* cited by examiner

*Primary Examiner*—Brian J Davis
(74) *Attorney, Agent, or Firm*—Oblon, Spivak, McClelland, Maier & Neustadt, L.L.P.

(57) ABSTRACT

The present invention relates to a process for producing a tertiary amine from its corresponding primary or secondary amine and alcohol as the raw materials by using a film type catalyst. Disclosed is a process for producing a tertiary amine from an alcohol and a primary or secondary amine, which including conducting the reaction, while circulating a reaction solution at least 3 times/hour in a reactor loaded with a film type catalyst in an external circulating line ancillary to a tank.

5 Claims, 1 Drawing Sheet

PROCESS FOR PRODUCTION OF TERTIARY AMINES

FIELD OF THE INVENTION

The present invention relates to a process for producing a tertiary amine from its corresponding primary or secondary amine and an alcohol as the raw materials by using a film type catalyst.

BACKGROUND OF THE INVENTION

Many industrial reactions are carried out in a mixing tank type reactor using solid catalyst slurry. These reactions are carried out by contacting a reactive gas, for example, hydrogen, ammonia or the like, with liquid in the presence of the catalyst. After the reaction is finished, generally the catalyst is removed by filtration to collect the reaction product.

However, a slurried catalyst has problems in safety, increase in waste material, operability and productivity. For example, there are problems that many of catalysts are spontaneously combustible, so powder and slurry catalysts must be handled with care, and the catalyst must be removed by filtration etc. in order to collect the reaction product, thus leading to complex facilities and operation.

As a process that requires neither a mixing operation by stirring or gas bubbling nor filtration separation of a catalyst, there can be mentioned a fixed-bed system. As to forms of a catalyst for use in the fixed-bed system, a molded catalyst of a pellet shape, noodle shape, or tablet shape has been well known conventionally. By subjecting powdery material having a catalyst activity to molding processing by such method as compression or extrusion into the above-mentioned form, a construction having an infinite number of fine pores therein is formed thereby satisfying both of the catalyst configuration and great surface area. For example, such technique is disclosed in JP-A 6-211754.

According to the reaction system, such problem as handleability of the catalyst and waste material can be solved, but there are many reactions to which the system can not be applied. For example, there were cases where temperature control was troublesome in reactions accompanied with absorption or generation of heat, and uneven liquid-gas distribution in a reactor sometimes resulted in an insufficient reaction percentage or many side reactions caused by local concentration gradient.

In tertiary amination reaction, when trying to obtain a reaction product at a high reaction percentage using the molded catalyst described in JP-A 6-211754, undesirable byproducts are generated in not small amounts. The byproduct includes not only wax or an aldol condensate generated by a side reaction of alcohol as the raw material, but also a tertiary amine generated as byproduct from ammonia, primary or secondary amine due to disproportionation of primary or secondary amine. Although various improvements have been carried out for practicing the technique highly selectively by suppressing formation of such byproducts, it has been difficult to practice this reaction highly selectively by an easy process.

JP-A 2003-176255 discloses a reactor in which a catalyst metal is adhered on the surface of monolith. It is noted that this reactor has an advantage that in a hydrogenation reaction between a gas and liquid, mass transfer is accelerated compared with a fixed-bed packed reactor of a conventional type, because the pressure drop of the reactor is small and the velocity of the gas and liquid can be made large.

JP-A 2002-35569 discloses a method of gas/liquid reaction in which a liquid and gas are fed as a liquid/gas mixture from a tank to a monolith catalyst reactor and then a reaction product drawn from the outlet is circulated in a tank. Reaction raw materials and reactants can be heated and cooled separately from the catalyst, and thus there are noted advantages such as minimization of byproduct formation and of catalyst inactivation.

SUMMARY OF THE INVENTION

The present invention provides a process for producing a tertiary amine from an alcohol and a primary or secondary amine, which includes conducting the reaction, while circulating a reaction solution at least 3 times/hour in a reactor loaded with a film type catalyst, the reactor provided in an external circulating line ancillary to a tank (hereinafter referred to as a buffering tank).

DETAILED DESCRIPTION OF THE INVENTION

In JP-A 2003-176255 supra, the reaction of a compound containing a nitrogen atom is contemplated, but the reaction expressly provided therein is only a reaction with a simple mechanism such as hydrogenation. Other examples disclosed therein are directed to limited uses mainly in hydrogenation reaction, and there is no example wherein the reactor is applied to a reaction having extremely complex mechanism, such as a reaction of an alcohol with a primary or secondary amine as the starting material to give the corresponding tertiary amine in higher yield.

In JP-A 2002-35569 supra, a wide variety of reactions such as hydrogenation and oxidation of organic compounds have been contemplated, but in the Examples, only the mass transfer rate of oxygen with an aqueous solution of sodium sulfite is measured, and other reactions are not specifically described. There is no description on the number of circulations per hour.

The present invention relates to a process for producing a tertiary amine from its corresponding primary or secondary amine and alcohol as the raw materials by using a film type catalyst, wherein a tertiary amine is produced efficiently in high yield.

According to the process of the present invention, an intended tertiary amine can be obtained efficiently in high yield by a simple process not requiring any separation operation of the catalyst.

Examples of the alcohol as a raw material for use in the process for producing a tertiary amine according to the present invention include linear or branched, saturated or unsaturated aliphatic alcohols having 8 to 36 carbon atoms. Specific examples of such alcohols include octyl alcohol, lauryl alcohol, myristyl alcohol, stearyl alcohol, behenyl alcohol, oleyl alcohol, mixed alcohols thereof, Ziegler alcohol obtained by the Ziegler method, and an oxo alcohol and a Guelbet alcohol obtained by the oxo method.

Examples of the primary or secondary amine as a raw material for use in the process for producing a tertiary amine according to the present invention include aliphatic primary or secondary amines, including methylamine, dimethylamine, ethylamine, diethylamine, dodecylamine or didodecylamine.

The tertiary amine obtained from the corresponding alcohol and primary or secondary amine as raw materials is an amine wherein a hydrogen atom bound to the nitrogen atom of the primary or secondary amine is substituted by an alkyl group and/or an alkenyl group derived from the alcohol. For example, the tertiary amine obtained from lauryl alcohol and dimethylamine is N-dodecyl-N,N-dimethylamine which is distinguished from tertiary amine byproducts N,N-didodecyl-N-methylamine and N,N,N-tridodecylamine formed by reaction between methylamine generated by disproportionation of dimethylamine and ammonia.

The film type catalyst for use in the present invention refers to a catalyst in the form of a thin film having a thickness of 500 µm or less, differing from a conventional packed-bed catalyst irregular in shape having several millimeters or thereabout. The process of transferring the reactants and the product in the inside of the catalyst is governed by diffusion, and the distance is reduced to 500 µm or less, whereby the mass transfer between the inside and outside of the catalyst can be promoted thereby effectively utilizing the whole of the catalyst and simultaneously suppressing the excessive reaction of the intermediate reaction product in the inside of the catalyst. The thickness of the film-type catalyst is particularly preferably 100 µm or less, more preferably 50 µm or less, in order to significantly increase the reaction activity per catalyst unit weight. The lower limit of the thickness is preferably 0.01 µm or more, even more preferably 1 µm or more, in order to secure the strength of the catalyst layer and attain durability of the strength thereof.

The structure of the film-type catalyst includes various structures depending on the shape of a reactor. For example, a catalyst coating layer formed on a wall in a tube, a catalyst formed in a tube in the form of a thin plate by which the tube is divided in an axial direction into a plurality of flow paths, etc. are mentioned and can be used preferably in a tubular flow reactor. The catalyst may be a catalyst coating layer or the like formed on the surface of an open fin-shaped flat plate arranged in a tank and can be preferably used in a tank reactor. In any cases, the catalyst is preferably structured such that supply of the reactants to the catalyst and recovery of the product from the catalyst can easily occur. The surface of the catalyst where supply of the reactants to the catalyst and recovery of the product from the catalyst occur is desirably as large as possible for efficient progress of the reaction. For achieving the above requirement, it is preferable to use the film-shaped catalyst arranged in a structure having assembled tubes each having an inner diameter of several millimeters to several ten millimeters or in the inner wall of a honeycomb structure having several ten to several hundred cells per square inch.

For forming the film-type catalyst in the various structures, there is for example a method of forming the catalyst active substance itself into a honeycomb structure, but from the viewpoint of satisfying both thin catalyst layer and high mechanical strength, the film-type catalyst is preferably fixed on the surface of a support. The support for the film-type catalyst is preferably a metal foil. There is for example a method wherein a coating layer containing the catalyst active substance is formed on the surface of a metallic or other rigid, tubular, planar or honeycomb support to produce the film-type catalyst. As the coating method, it is possible to use conventionally known methods including not only physical deposition such as sputtering etc., chemical deposition, and dipping into a solution, but also various coating methods with a binder, such as blade coating, spray coating, dip coating, spin coating, gravure coating and die coating.

The active substance constituting the film-type catalyst is not particularly limited and may be a known active substance, and generally a metal such as copper can be preferably used, and a metal containing copper is more preferably used. For example, use is made of Cu alone or a metal containing 2 components, that is, Cu and a transition metal element such as Cr, Co, Ni, Fe or Mn, preferably a metal containing Cu and Ni. Further, a metal containing 3 components or more is also preferably used. Further, the metal supported on a carrier such as silica, alumina, titania or zeolite can also be used.

The film-type catalyst can contain a binder which does not act as an active substance but fixes the active substance to form the film-type catalyst. The binder includes high-molecular or inorganic compounds which are durable to the reaction environment, do not adversely affect the reaction system and have not only a property of binding particles of the active substance together or binding the active substance to the surface of a support but also properties such as chemical resistance and heat resistance. Examples of the binder include cellulose resin such as carboxymethyl cellulose and hydroxyethyl cellulose, fluorine-based resin such as polytetrafluoroethylene and polyvinylidene-fluoride, high-molecular compounds such as urethane resin, epoxy resin, polyester resin, phenol resin, melamine resin, silicone resin, polyvinyl alcohol, polyimide resin and polyimide amide resin, and sol of inorganic compound such as silica and alumina.

The internal structure of the film-type catalyst depends significantly on the type of the active substance constituting the catalyst and on the method of preparing the catalyst, and may form a dense continuous phase or may be porous. For example, when the catalyst is a thin film formed on the surface of a support by sputtering and chemical vapor deposition, the catalyst can have a dense continuous phase, while when the powdery active substance is used to form a thin film on the surface of a support by wet or dry coating, the catalyst can be porous.

In the present invention, a reactor loaded with the film-type catalyst described above is arranged in an external circulating line ancillary to a buffering tank, and a reaction solution is circulated at least 3 times/hour in the reactor, whereby the reaction of an alcohol with a primary or secondary amine is carried out.

In the present invention, the buffering tank means a container for storing the raw materials necessary for the reaction and/or the reaction product generated by the reaction, and, if necessary, it is also possible to separate the reaction product and/or unreacted raw materials discharged from the reactor to carry out gas/liquid separation into a gas component and a liquid component in the buffering tank and remove the gas component to the outside of the system. There is no particular limitation on the buffering tank provided that it is of a commonly used type, and the buffering tank is preferably not loaded with the catalyst. The buffering tank may have a jacket or an internal coil for heating or cooling the raw material or reactants. Further, the buffering tank may have an agitator for making the liquid uniform, or adversely may have a structure with no agitation, the structure being provided with a partition board in the buffering tank so as to enhance plug flow of the reaction liquid.

The process of the present invention, as compared with the case where a reaction tank itself is loaded with the film type catalyst, but not provided with a buffering tank, does not require considerable alterations to the reaction tank, and maintenance such as exchange of the film type catalyst etc. is easy. In the case of a reaction facility already having an external circulating line, a reactor loaded with the film type catalyst can be easily installed in the external circulating line. As the reactor loaded with the film type catalyst, various reactors including those known in the art can be used. For example, the film type catalyst after being rolled as a cylinder or processed into strips may be loaded inside of a tubular reactor. The film type catalyst also may be loaded in a tube or shell portion of a shell & tube heat exchanger type. In this instance, the temperature of the reaction portion can be controlled by flowing a heat medium on the tube side or shell side onto which the film type catalyst has not been loaded. In the case of a tubular flow reactor, it is possible to allow the reaction to proceed in a continuous system by using a system where reactants are fed to the film type catalyst inside the tube while the reaction product is collected continuously to achieve a circular feeding.

BRIEF DESCRIPTION OF THE DRAWINGS

In FIG. 1, 1 is a tubular reactor loaded with the film type catalyst, 2 is a buffering tank, 3 is a pump for external circulation, 4 is a conduit pipe for external circulation, 5 is a conduit pipe for a packed column, and 6 is a packed column.

Figure 1:
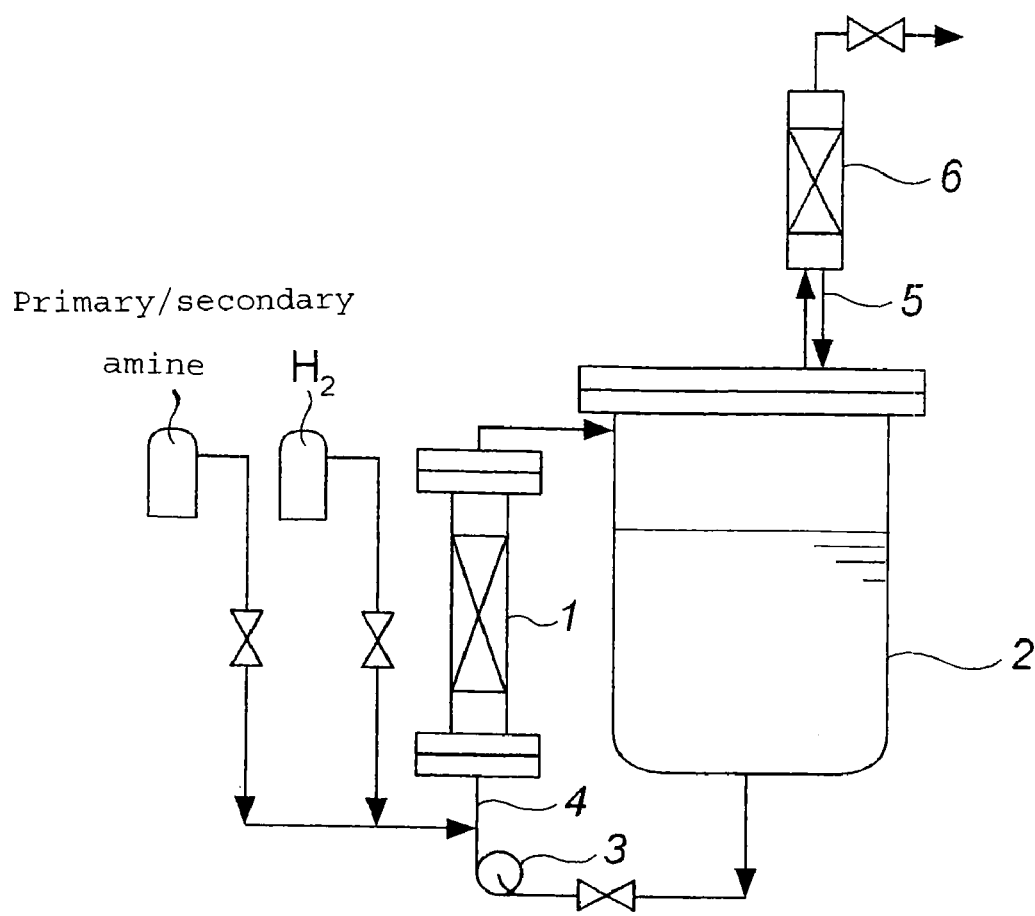
FIG. 1 is a schematic view showing one example of the reaction apparatus used in the present invention.

The tubular reactor 1 is a perpendicular round tube type fixed-bed reactor loaded therein with the film type catalyst and capable of controlling the temperature by heating from the outside. The buffering tank 2 is a storage tank of the liquid reactants and/or a mixture of the reaction products, which are circulated between the buffering tank 2 and the reactor 1 by pump 3. Through the conduit pipe 4, the reactants and/or a mixture of the reaction products, and gaseous primary or secondary amine and hydrogen gas are fed continuously from the lower end of the reactor 1, while the unreacted reactants and/or a mixture of reaction products and hydrogen gas are collected continuously from the upper end and introduced into the buffering tank 2. Through the conduit pipe 5, unreacted gaseous primary or secondary amine and moisture are discharged continuously. Not only those described above, but also vapor or mist-like components of alcohol and/or generated tertiary amine etc. are sometimes included in the components discharged from the conduit pipe 5, and these components are condensed and liquidized in the packed tower 6 and returned to the buffering tank 2, and remaining gas component is discharged to the outside of the system. The inside of the reaction system is maintained at around ordinary pressure.

The method of feeding a reaction solution to the reactor 1 may be carried out in an upflow system as shown in FIG. 1, or conversely may be in a downflow system. The temperature of the reactor is preferably controlled with a jacket or a piping for heat exchange arranged inside, as is usually carried out.

In the reaction of an alcohol with a primary or secondary amine in the present invention, the number of external circulations of the reaction solution per hour is at least 3/hr, preferably at least 4/hr, more preferably at least 5/hr, from the viewpoint of suppressing side reactions. From the viewpoint of reducing energy necessary for circulation, the number of external circulations of the reaction solution per hour is preferably up to 200/hr, more preferably up to 100/hr.

The number of external circulations of the reaction solution per hour can be controlled by the amount of the raw materials loaded and the circulating volume of pump 3 for external circulation in FIG. 1. The number of external circulations per hour may be changed by reaction time, for example by increasing the time in an initial stage of the reaction and decreasing the time in a terminal stage of the reaction.

The conditions where an alcohol is reacted with a primary or secondary amine vary depending on the reactants, the product and the type of the catalyst. The reactants may be present in a gaseous or liquid phase. When a gaseous phase is present in the reaction system, the reaction of the reactants in an atmosphere of hydrogen, nitrogen and/or a rare gas is preferable for maintaining the catalyst activity. When the alcohol and the primary or secondary amine are present in different phases respectively in a reaction system of gaseous/liquid two phases, promotion of mass transfer between the two phases by gas bubbling in the liquid is desired. The mass transfer can also be promoted by feeding the reactants in a gaseous/liquid mixed phase to the reaction system where a thin flow path having a diameter of several millimeters or less is formed from the film-type catalyst.

The pressure in the system is desirably not significantly higher than normal pressures. Although the reaction temperature varies depending on the type of the catalyst, the reaction is preferably conducted at a temperature of 150 to 300° C. Water produced as a byproduct in the reaction is discharged from the reaction system, whereby progress of the reaction can be promoted and the catalyst activity can be maintained.

According to the process of the present invention, an intended tertiary amine from a primary or secondary amine and an alcohol as the raw materials can be obtained efficiently at a high yield by a simple process not requiring any special mixing operation, nor separation operation of the catalyst.

EXAMPLES

The present invention is described more in details by reference to the Examples below. The Examples are merely illustrative of the present invention and are not intended to limit the present invention.

Production Example 1

Production of Film Type Catalyst A

A film type catalyst A in which a powdery catalyst was fixed using phenol resin as a binder was prepared as follows.

A flask having a volume of one litter was charged with synthetic zeolite and then with a solution prepared by dissolving copper nitrate, nickel nitrate and ruthenium chloride in water such that Cu:Ni:Ru=4:1:0.01 in the molar ratio of metal atoms, and then the mixture was heated under stirring. At 90° C., an aqueous 10% sodium carbonate solution was gradually dropped into it while the pH was controlled at 9 to 10. After 1-hour aging, precipitates were filtered off, washed with water, then dried at 80° C. for 10 hours and calcined at 600° C. for 3 hours to give a powdery catalyst. The obtained powdery catalyst contained the metal oxides at a ratio of 50% by weight and the synthetic zeolite at a ratio of 50 by weight.

To 100 parts by weight of the powdery catalyst described above, phenol resin (PR-9480, manufactured by Sumitomo Bakelite Co., Ltd., nonvolatile content: 58%) was added as a binder such that the nonvolatile content of the phenol resin became 47.7 parts by weight. Then, 2-butanone was added as solvent thereto such that solids content (the powdery catalyst and non-volatiles in the phenol resin) became 55. The mixture was preliminarily mixed by a Disper for 10 minutes, then mixed and dispersed at 1500 rpm for 70 minutes in a basket mill (SS-3, manufactured by ASADA IRON WORKS, Co., Ltd., charged with 1900 g (800 mL) titania beads having a diameter of 1.4 mm) to form a coating. A copper foil (thickness 40 µm, 6.5 cm×410 cm×1 sheet) was used as a support, and the coating was applied by a bar coater on both sides of the support and dried at 150° C. for 30 seconds. Half of the resulting dried specimen was corrugated in a corrugate form, stacked alternately with the remaining planar catalyst specimen, wound together, and cured at 150° C. for 90 minutes, to fix the film-type catalyst on both sides of the copper foil. The thickness of the resulting film-type catalyst on one side, excluding the thickness of the copper foil, and the total mass thereof excluding the copper foil are as shown respectively in Table 1.

Production Example 2

Production of Film Type Catalyst B

A film type catalyst B in which a powdery catalyst was fixed using phenol resin as a binder was prepared as follows.
Phenol resin (PR-9480 with 58% non-volatiles, manufactured by Sumitomo Bakelite Co., Ltd.) was added as a binder to 100 parts by weight of the powdery catalyst prepared according to Production Example 1, such that the content of non-volatiles in the phenol resin became 47.7 parts by weight. Then, 4-methyl-2-pentanone was added as solvent thereto such that the solids content (the powdery catalyst and non-volatiles in the phenol resin) became 55%. The mixture was preliminarily mixed by a Disper for 10 minutes, then mixed and dispersed at 1500 rpm for 70 minutes in a basket mill (SS-3 manufactured by ASADA IRON WORKS, Co., Ltd., charged with 800 mL (1900 g) titania beads of 1.4 mm in diameter) to form a coating. A copper foil (thickness 40 μm, 0.3 m×36 cm) was used as a support, and the coating was applied by a gravure coater on both sides of the support and dried at 150° C. for 30 seconds. The dried product was cut into 27 cm×429 cm×16 sheets. Half of the resulting dried specimens were corrugated in a corrugate form and stacked alternately with the remaining planar catalyst specimens. They were loaded in a cylindrical holder for use in the perpendicular round tubular fixed-bed reactor 1 shown in FIG. 1. They were then cured at 150° C. for 90 minutes, to fix the film-type catalyst on both sides of the copper foil. The thickness of the resulting film-type catalyst on one side, excluding the thickness of the copper foil, and the total mass thereof excluding the copper foil are as shown respectively in Table 1.

Production Example 3

Production of Film Type Catalyst C

A film type catalyst C in which a powdery catalyst was fixed using phenol resin as a binder was prepared as follows.
To 100 parts by weight of the powdery catalyst produced according to Production Example 1, phenol resin (PR-9480, manufactured by Sumitomo Bakelite Co., Ltd., nonvolatile content: 58%) was added as a binder such that the nonvolatile content of the phenol resin became 33.3 parts by weight. Then, 4-methyl-2-pentanone was added as solvent thereto such that solids content (the powdery catalyst and non-volatiles in the phenol resin) became 55%. The mixture was preliminarily mixed by a Disper for 10 minutes, then mixed and dispersed at 1500 rpm for 70 minutes in a basket mill (SS-3 manufactured by ASADA IRON WORKS Co., Ltd., charged with 1900 g (800 mL) titania beads having a diameter of 1.4 mm,) to form a coating. A copper foil (thickness 40 μm, 6.5 cm×420 cm×1 sheet) was used as a support, and the coating was applied by a bar coater on both sides of the support and dried at 150° C. for 30 seconds. Half of the resulting dried specimen was corrugated in a corrugate form, stacked alternately with the remaining planar catalyst specimen, wound together, and cured at 150° C. for 90 minutes, to fix the film-type catalyst on both sides of the copper foil. The thickness of the resulting film-type catalyst on one side, excluding the thickness of the copper foil, and the total mass thereof excluding the copper foil are as shown respectively in Table 1.

In Examples 1 to 4 below, N-dodecyl-N,N-dimethylamine (hereinafter referred to as "DM derivative") was produced from lauryl alcohol and dimethylamine as raw materials by using the fixed-bed type flow reaction apparatus shown in FIG. 1. In the Examples below, "%" indicates "% by weight" unless otherwise noted.

Example 1

The reactor 1 having an inner diameter of 29.5 mm was loaded with the film type catalyst A obtained in Production Example 1. The loaded portion of the film type catalyst had a volume of 0.27 L, and a plurality of flow paths each having a sectional area of about 0.1 cm$^2$ running in the axial direction of the reactor 1 were formed from the film-type catalyst. 1.0 kg lauryl alcohol (KALCOL 20 manufactured by Kao Corporation) was introduced into the buffering tank 2, and while a hydrogen gas was fed at a flow rate of 20 L/hr in terms of volume under standard conditions, circulation of the liquid between the buffering tank 2 and the reactor 1 was carried out 5.1 times/hr. The number of liquid circulations can be determined from the volume (V (L)) of the starting alcohol loaded and the quantity (Q (L/hr)) of external circulation, by the following equation (1):

$$\text{Number of liquid circulations (number/hr)} = Q/V \qquad (1)$$

By conversion of 1.0 kg starting alcohol by using a density of 0.683 (g/cm$^3$) at 220° C., V=1.46 (L) was determined and used together with Q=7.5 (L/hr) to determine the number of liquid circulations in Example 1, by the following equation (1):

$$\text{Number of liquid circulations} = 7.5/1.46 = 5.1 \text{ (times/hr)}$$

The internal temperature of the reactor 1 was raised to 220° C., and then the reaction was initiated at 220° C. by feeding dimethylamine. The feed volume of dimethylamine was regulated in accordance with the progress of the reaction, which was 79 g/hr on reaction time average. After 5.9 hours from the beginning of the reaction, feeding of dimethylamine was terminated, and the whole volume of the liquid inside the buffering tank 2 and the reactor 1 was drawn. The liquid was analyzed with gas chromatography. The result of quantification by the area percentage method showed 1% of unreacted lauryl alcohol, 89.7% of generated DM derivative, and 7.8% of N,N-didodecyl-N-methylamine (referred to hereinafter as M2 derivative) that is a tertiary amine produced as byproduct. N,N,N-tridodecylamine was not detected.

Example 2

The same operation as in Example 1 was carried out except that the circulation of liquid between the buffering tank 2 and reactor 1 was carried out 3.4 times/hr. Then, the internal temperature of the reactor 1 was raised to 220° C. and the reaction was initiated by feeding dimethylamine. The feed volume of dimethylamine was regulated in accordance with the progress of the reaction, which was 86 g/hr on reaction time average. After 6.2 hours from the beginning of the reaction, feeding of dimethylamine was terminated, and the whole volume of the liquid inside the buffering tank 2 and the reactor 1 was drawn. The liquid was analyzed by gas chromatography in the same manner as in Example 1. The result showed 1% of unreacted lauryl alcohol, 87.4% of generated DM derivative, and 9.5% of M2 derivative that is a tertiary amine produced as byproduct.

Example 3

The reactor 1 having an inner diameter of 101 mm was loaded with the film type catalyst B obtained in Production Example 2. The loaded portion of the film type catalyst had a volume of 17.4 L, and a plurality of flow paths each having a sectional area of about 0.1 cm$^2$ running in the axial direction of the reactor 1 were formed from the film-type catalyst. 46.1 kg lauryl alcohol (KALCOL 20 manufactured by Kao Corporation) was introduced into the buffering tank 2, and while a hydrogen gas was fed at a flow rate of 922 L/hr in terms of volume under standard conditions, circulation of the liquid between the buffering tank 2 and the reactor 1 was carried out 10.2 times/hr. The internal temperature of the reactor 1 was raised to 220° C., and then the reaction was initiated at 220° C. by feeding dimethylamine. The feed volume of dimethylamine was regulated in accordance with the progress of the reaction. After 3.8 hours from the beginning of the reaction, feeding of dimethylamine was terminated, and the whole volume of the liquid inside the buffering tank 2 and the reactor 1 was drawn. The liquid was analyzed by gas chromatography. The result of quantification by the area percentage method showed 1% of unreacted lauryl alcohol, 90.4% of generated DM derivative, and 7.4% of M2 derivative that is a tertiary amine produced as byproduct. N,N,N-tridodecylamine was not detected.

Example 4

The same operation as in Example 3 was carried out except that the circulation of liquid between the buffering tank 2 and reactor 1 was carried out 3.4 times/hr. Then, the internal temperature of the reactor 1 was raised to 220° C. and the reaction was initiated by feeding dimethylamine. The feed volume of dimethylamine was regulated in accordance with the progress of the reaction. After 3.8 hours from the beginning of the reaction, feeding of dimethylamine was terminated, and the whole volume of the liquid inside the buffering tank 2 and the reactor 1 was drawn. The liquid was analyzed by gas chromatography in the same manner as in Example 3. The result showed 1% of unreacted lauryl alcohol, 89.9% of generated DM derivative, and 8.2% of M2 derivative that is a tertiary amine produced as byproduct.

In Example 5 below, N,N-didecyl-N-methylamine (referred to hereinafter as M2 derivative) was produced from n-didecyl alcohol and monomethylamine as raw materials by using the fixed-bed type flow reaction apparatus shown in FIG. 1. In the Example below, "%" indicates "% by weight" unless otherwise noted.

Example 5

The reactor having an inner diameter of 29.5 mm was loaded with the film-type catalyst C obtained in Production Example 3. The loaded portion of the film type catalyst had a volume of 0.27 L, and a plurality of flow paths each having a sectional area of about 0.1 cm$^2$ running in the axial direction of the reactor 1 were formed from the film-type catalyst. 0.6 kg n-decyl alcohol (KALCOL 10 manufactured by Kao Corporation) was introduced into the buffering tank 2, and while a hydrogen gas was fed at a flow rate of 12 L/hr in terms of volume under standard conditions, circulation of the liquid between the buffering tank 2 and the reactor 1 was carried out 8.8 times/hr.

The internal temperature of the reactor 1 was raised to 180° C., and then the reaction was initiated at 185° C. by feeding monomethylamine. The feed volume of monomethylamine was regulated in accordance with the progress of the reaction, which was 18 g/hr on reaction time average. After 4.5 hours from the beginning of the reaction, feeding of monomethylamine was terminated, and the whole volume of the liquid inside the buffering tank 2 and the reactor 1 was drawn. The liquid was analyzed by gas chromatography. The result of quantification by the area percentage method showed 0.3% of unreacted n-decyl alcohol, 93.6% of generated M2 derivative, 0.7% of N-decyl-N,N-dimethylamine (referred to hereinafter as DM derivative) that is a tertiary amine produced as byproduct, and 1.2% N,N,N-tridecylamine (referred to hereinafter as T derivative).

TABLE 1

| | | | Example 1 | Example 2 | Example 3 | Example 4 | Example 5 |
|---|---|---|---|---|---|---|---|
| Film type catalyst | Kind | | Catalyst A | | Catalyst B | | Catalyst C |
| | Thickness*[1] | (μm) | 4.9 | | 5.4 | | 32 |
| | Amount of catalyst*[2] | (g-film type catalyst) | 5.0 | | 384 | | 21 |
| | Film area | (m$^2$-film) | 0.53 | | 37 | | 0.55 |
| Reactor | Volume of the portion loaded with the film type catalyst | (L) | 0.27 | 0.27 | 17.4 | 17.4 | 0.27 |
| | Internal diameter | (mm) | 29.5 | 29.5 | 101 | 101 | 29.5 |
| Reaction condition | Starting alcohol | Kind | Lauryl alcohol | | | | Decyl alcohol |
| | | (kg-alcohol) | 1.0 | 1.0 | 46.1 | 46.1 | 0.6 |
| | External circulation flow rate | (L/Hr) | 7.5 | 5.0 | 692 | 231 | 7.5 |
| | Number of external circulations | (times/Hr) | 5.1 | 3.4 | 10.2 | 3.4 | 8.8 |
| | Temperature in the reactor | (° C.) | 220 | 220 | 220 | 220 | 185 |
| | Hydrogen flow rate | (NL/Hr) | 20 | 20 | 922 | 922 | 12 |
| | Dimethylamine flow rate | (g/Hr) | 79 | 86 | 3500 | 3500 | — |
| | Monomethylamine flow rate | (g/Hr) | — | — | — | — | 18 |
| | Time | (Hr) | 5.9 | 6.2 | 3.8 | 3.8 | 4.5 |

TABLE 1-continued

|  |  |  | Example 1 | Example 2 | Example 3 | Example 4 | Example 5 |
|---|---|---|---|---|---|---|---|
| Result of reaction | DM derivative*[3] | (weight %) | 89.7 | 87.4 | 90.4 | 89.9 | 0.7 |
|  | M2 derivative*[4] | (weight %) | 7.8 | 9.5 | 7.4 | 8.2 | 93.6 |
|  | T derivative*[5] | (weight %) | 0.0 | 0.0 | 0.0 | 0.0 | 1.2 |

*[1]Thickness of the catalyst layer excluding the copper foil
*[2]Amount of the film catalyst excluding the copper foil
*[3]N-alkyl-N,N-dimethylamine
*[4]N,N-dialkyl-N-methylamine
*[5]N,N,N-trialkylamine
(The alkyl in Examples 1 to 4 is dodecyl, and the alkyl in Example 5 is decyl.)

The invention claimed is:

1. A process for producing a tertiary amine comprising:
reacting an alcohol and a primary or secondary amine in a reaction solution in a reactor loaded with a film type catalyst provided in an external circulating line ancillary to a tank,
while circulating the reaction solution at a rate of at least 3 times/hour in the reactor.

2. The process for producing a tertiary amine according to claim 1, wherein the film type catalyst is fixed on the surface of a support and the thickness of the catalyst is 0.01 to 500 μm.

3. The process for producing a tertiary amine according to claim 1, wherein the reactor is a tubular flow reactor.

4. The process for producing a tertiary amine according to claim 1, wherein the alcohol is a linear or branched, saturated or unsaturated aliphatic alcohol having 8 to 36 carbon atoms.

5. The process for producing a tertiary amine according to claim 1, wherein the primary or secondary amine is an aliphatic primary or secondary amine.

* * * * *